United States Patent [19]

Grossman et al.

[11] Patent Number: 5,162,557
[45] Date of Patent: * Nov. 10, 1992

[54] RUTHENIUM AROMATIC POLYCARBOXYLATES

[75] Inventors: Richard F. Grossman, Shelton, Conn.; David M. Tanno, Richmond Heights, Ohio

[73] Assignee: Synthetic Products Company, Cleveland, Ohio

[*] Notice: The portion of the term of this patent subsequent to Jun. 25, 2008 has been disclaimed.

[21] Appl. No.: 688,244

[22] Filed: Apr. 22, 1991

Related U.S. Application Data

[63] Continuation-in-part of Ser. No. 356,638, May 24, 1989, Pat. No. 5,026,888, which is a continuation of Ser. No. 224,828, Jul. 27, 1988, abandoned.

[51] Int. Cl.$^5$ .............................................. C07F 15/00
[52] U.S. Cl. .................................... 556/136; 437/1; 437/179; 437/201
[58] Field of Search ................... 556/136; 437/1, 179, 437/201

[56] References Cited

U.S. PATENT DOCUMENTS

| | | | |
|---|---|---|---|
| 2,280,474 | 4/1942 | Byrkit et al. | 556/106 |
| 2,355,240 | 8/1944 | Reiff | 556/136 |
| 3,314,919 | 4/1967 | Most | 260/45.85 |
| 3,674,894 | 7/1972 | Economy et al. | 260/875 |
| 3,754,986 | 8/1973 | Perez-Albuerne | 437/1 X |
| 3,884,825 | 5/1975 | Lindblad et al. | 252/62.1 |
| 3,973,982 | 8/1976 | Bingham | 106/298 |
| 4,039,515 | 8/1977 | Rebhan et al. | 260/75 |
| 4,096,109 | 6/1978 | Watanabe | 260/40 |
| 4,101,523 | 7/1978 | Watanabe | 528/309 |
| 4,198,458 | 4/1980 | Mitsuishi | 428/212 |

OTHER PUBLICATIONS

Svoboda et al, "Ruthenium Carboxylates Bonded to Polyester", Chem. Abstracts, 96(16); 123559d, 1980.

*Primary Examiner*—Arthur C. Prescott
*Attorney, Agent, or Firm*—Wood, Herron & Evans

[57] ABSTRACT

Ruthenium aromatic polycarboxylates from the class consisting of ruthenium isophthalate, ruthenium trimesate, ruthenium trimellitate, ruthenium pyromellitate and ruthenium 5-sulfonate-1,3-isophthalate have been prepared and have been found to be especially suitable as semiconductors.

3 Claims, No Drawings

RUTHENIUM AROMATIC POLYCARBOXYLATES

RELATED INVENTION

This application is a continuation-in-part of application Serial No. 07/356,638, filed May 24, 1989, now U.S. Pat. No. 5,026,888 which in turn is a continuation of application Ser. No. 07/224,828, filed July 27, 1988, now abandoned.

BACKGROUND OF THE INVENTION

Numerous metal salts of terephthalic acid have been reported in the literature with a broad range of utilities, most often as additives to polymeric compositions. For example, in U.S. Pat. No. 3,314,919 terephthalates of calcium, barium, manganese, zinc and cadmium were reportedly prepared and incorporated into textile fibers for the improvement of mechanical properties of such fibers. Other examples of patent literature disclosing metal terephthalates, principally in polymeric compositions, include U.S. Pat. Nos. 3,674,894; 3,884,825; 3,973,982; 4,039,515; 4,096,109; 4,101,523; 4,198,458 and others. Other literature has reported upon metal terephthalates and study of their various properties, but delineation of details of such studies are not considered to be relevant to the subject matter of this invention.

SUMMARY OF THE INVENTION

This invention is directed to new metal salts of ruthenium, specifically ruthenium carboxylates. Ruthenium terephthalate, ruthenium isophthalate, ruthenium trimesate, ruthenium trimellitate, ruthenium pyromellitate and ruthenium 5-sulfo-nate-1,3-isophthalate have been prepared. These compounds have been found to have very low volume resistivities that makes them especially suitable for use as semiconductors.

DETAILED DESCRIPTION

A. Preparation of Ruthenium Terephthalate

A stoichiometric excess of terephthalic acid was dissolved in 10% sodium hydroxide aqueous solution. To this solution was added 10 grams of ruthenium trichloride dissolved in 100 mls water, resulting in a black precipitate. The precipitate was filtered, washed with water and dried at 100° C. to constant weight. Elemental analysis of this product yielded 23.7% ruthenium, 44.4% carbon and 1.84% hydrogen. This corresponds to the formula $Ru(C_8H_4O_4)_2$; theoretically 23.5% Ru, 44.7% C and 1.73% H. The course of the reaction may have involved air oxidation of ruthenium from the (III) to the (IV) valence state, inasmuch as these valence states are very close energetically.

Samples of the prepared ruthenium terephthalate were compacted into flat plates of 10 mils in thickness and 3.5 cms radius at room temperature between polished steel plates at 20,000 psi in a laboratory press. Volume resistivity was determined using an Associated Research, inc. Model 2850 megohm bridge. The volume resistivity of ruthenium terephthalate samples was on the order of 100 to 200 ohm-cms. Upon irradiation at a range of about 4 inches with a 150 watt near-UV and visible source, Philips "Agro-Lite", the volume resistivity dropped to 20–40 ohm-cms, indicating that the semiconductance of ruthenium terephthalate is light sensitive. The dielectric constant of the compound was too high to be measured by a capacitance bridge and this is indicative of the semiconductive properties of the compound.

B. Preparatioon of Ruthenium Isophthalate

Ruthenium isophthalate was prepared and tested as described above in the case of ruthenium terephthalate. Elementary analysis indicates $Ru(C_8H_4O_4)_2$ Ru; theor. 23.5, found 23.8; C, theor. 44.7, found 45.0; H, theor. 1.85, found 1.90. Thus, as with the terephthalate, reaction of $RuCl_3$ with sodium isophthalate solution in air yields an $Ru^{+4}$ not $Ru^{+3}$ product. Ruthenium isophthalate is a semiconductor having a volume resistivity of about 10 ohm-cm at room temperature. This salt decomposes at 85° C., as compared to 550° C. for the corresponding terephthalate.

C. Preparation of Ruthenium Trimesate

Ruthenium trimesate was prepared and tested as described above in the case of ruthenium terephthalate. Elementary analysis indicates a one-to-one Ru $(C_9H_3O_6)$. Ru, theor. 32.7, found 32.3; C, theor. 35.1, found 35.0; H, theor. 0.97, found 0.92%. Ruthenium trimesate is a semiconductor having a volume resistivity of about 1 ohm-cm at room temperature. This salt decomposes at 540° C. Although the metal/anion ratio is certainly one-to-one, it is not presently known whether this compound involves the $+3$ or $+4$ oxidation state of ruthenium (or both).

D. Preparation of Ruthenium Trimellitate

Ruthenium trimellitate was prepared and tested as described above in the case of ruthenium terephthalate. Elementary analysis again indicates a one-to-one $Ru(C_9H_3O_6)$. Ru, theor. 32.7, found 32.5; C, theor. 35.1, found 34.7; H, theor. 0.97, found 0.94%. Ruthenium trimellitate is a semiconductor having a volume resistivity of about 50 ohm-cm at room temperature.

E. Preparation of Ruthenium Pyromellitate

Ruthenium pyromellitate was prepared and tested as described above in the case of ruthenium terephthalate. Analysis again indicates a one-to-one $Ru(C_{10}H_2O_8)$. Ru, theor. 29.8 found 29.6; C, theor. 34.2, found 34.5; H, theor. 0.57, found 0.55%. Ruthenium pyromellitate is a semiconductor having a volume resistivity of about 20 ohm-cm at room temperature. This salt decomposes at 475° C.

F. Preparation of Ruthenium 5-Sulfonate-1,3-Isophthalate

Ruthenium 5-sulfonate-1,3-isophthalate was prepared and tested as described above by reacting the sodium salt of 5-sulfonate-1,3-isophthalate. Analysis indicates a one-to-one $Ru(C_8H_3SO_7)$. Ru, theor. 29.4, found 29.0; C, theor. 27.9, found 27.6; H, theor. 0.88, found 0.85%. Ruthenium 5-sulfonate-1,3-isophthalate is a semiconductor having a volume resistivity of about 1 ohm-cm at room temperature. This salt decomposes at 410° C.

On the basis of the above, there is a class of ruthenium salts of phenyl polycarboxylates having at least two carboxylate groups, and optionally a sulfonate group, in the 1,3; 1,4; 1,3,5; 1,2,4; or 1,2,4,5 positions that are polymeric with high resistance to thermal decomposition and are semiconductive. The class includes all polybasic aromatic acid anions except 1,2-disubstituted species because ruthenium o-phthalate is not a polymeric salt, does not have a high resistance to thermal decomposition and is not a semiconductor, rather it has a volume resistivity of $10^9$ ohm-cm.

For comparative purposes, typical metal terephthalates having high volume resistivities of $10^{12}$ to $10^{14}$ ohm-cm and dielectric constants of between 4 and 5 were tested. These values are given by Ca, Zn, Mg, Al, In, Pb, Cd, Sn(II), Fe(III), Sr, Hg, Co, Ni and Cu(II) terephthalates. Surprisingly, therefore, ruthenium aromatic polycarboxylates have unusually high dielectric constants and are excellent semiconductors in comparison to other metal terephthalate or similar salts.

What is claimed is:

1. A ruthenium aromatic polycarboxylate from the class consisting of ruthenium isophthalate, ruthenium trimesate, ruthenium trimellitate, ruthenium pyromellitate and ruthenium 5-sulfonate-1,3-isophthalate.

2. A semiconductor article containing as the semiconductive compound a ruthenium aromatic polycarboxylate selected from the class consisting of ruthenium isophthalate, ruthenium trimesate, ruthenium trimellitate, ruthenium pyromellitate and ruthenium 5-sulfonate-1,3-isophthalate.

3. A semiconductor article containing as the semiconductive compound a ruthenium phenyl polycarboxylate having the polycarboxylate groups in the phenyl nucleus in the 1,3; 1,4; 1,3,5; 1,2,4; or 1,2,4,5 positions.

* * * * *

UNITED STATES PATENT AND TRADEMARK OFFICE
CERTIFICATE OF CORRECTION

PATENT NO. : 5,162,557
DATED     : November 10, 1992
INVENTOR(S) : Richard F. Grossman et al It is certified that error appears in the above-identified patent and that said Letters Patent is hereby corrected as shown below:

Column 2, line 3, "Preparatioon   " should be --preparation--

Column 2, line 14, "decomposes at 85°C." should be ----decomposes at 485°C.--

Column 2, line 44, "theor. 29.8 found" should be --theor. 29.8, found--

Signed and Sealed this

Twenty-sixth Day of October, 1993

Attest:

BRUCE LEHMAN

*Attesting Officer*           *Commissioner of Patents and Trademarks*